United States Patent [19]
Erdman

[11] Patent Number: 6,048,347
[45] Date of Patent: Apr. 11, 2000

[54] LENS STORAGE AND FOLDING APPARATUS

[75] Inventor: Arthur G. Erdman, New Brighton, Minn.

[73] Assignee: Micro Medical Devices, Inc.

[21] Appl. No.: 08/847,983

[22] Filed: Nov. 1, 1996

Related U.S. Application Data

[60] Provisional application No. 60/007,198, Nov. 1, 1995, and provisional application No. 60/007,697, Nov. 29, 1995.

[51] Int. Cl.[7] ........................................ A61F 9/00
[52] U.S. Cl. ............................................. 606/107
[58] Field of Search ........................ 606/107, 1; 623/4, 623/6

[56] References Cited

U.S. PATENT DOCUMENTS

| 5,494,484 | 2/1996 | Feingold | 606/107 |
| 5,578,042 | 11/1996 | Cumming | 606/107 |

*Primary Examiner*—Michael Buiz
*Assistant Examiner*—Vy Q. Bui
*Attorney, Agent, or Firm*—Fish & Richardson P.C.

[57] ABSTRACT

An intraocular lens storage container includes a lens folding system for folding the lens and inserting it into a lens insertion device or other lens receiving chamber. The fold and insertion process requires no special training and results in the lens being positioned in a known orientation. Also, the possibility of damaging the lens is minimized.

14 Claims, 11 Drawing Sheets

LENS STORAGE AND FOLDING APPARATUS

This application claims benefit of provisional application 60/007,198, filed Nov. 1, 1995, and provisional application 60/007,697, filed Nov. 29, 1995.

FIELD OF THE INVENTION

The present invention relates to storing and folding an intraocular lens prior to implantation.

BACKGROUND AND SUMMARY

An intraocular lens (IOL) is implanted in an eye of a patient to enhance or restore vision. Many configurations of IOLs are known. The IOL and the haptics, which hold the IOL in the eye, come in many forms. Until recently, the IOLs were generally inflexible and required an incision approximately equal in length to the diameter of the lens to be implanted. For a number of medical and clinical reasons, however, the length of the incision should be minimized.

Recently, foldable IOLs have been developed. Various configurations of foldable IOLs exist and the materials used to make them vary. The foldable IOL permits the incision for implantation to be smaller than that required for previous IOLs (e.g., fifty percent smaller or less). The inventors recognized the substantial benefits of using a smaller incision without jeopardizing the quality of the IOL.

Procedures have been developed for folding an IOL prior to implantation. These procedures generally involve using forceps to fold the IOL while a second forceps holds the IOL, or the IOL is positioned on a mechanical device and gripped by forceps. Variations on this procedure have been developed by different ophthalmologists commensurate with their particular manual dexterity, surgical skills, and preference of instruments.

Tubular IOL insertion devices have been developed to assist the ophthalmologist in inserting a foldable IOL into a patient's eye. The IOL is folded manually as described above and loaded into the insertion device. The distal end of the insertion device is passed through an incision in the eye and the folded IOL is then pushed through the distal end and expelled from the insertion device into the capsulary bag of the eye. The IOL is then centered within the eye and held in place by the haptics. In a limited number of cases, the IOL must be sutured into a desired position.

Various problems may arise while removing the IOL from its sterile storage container, manually folding the IOL, manually placing the folded IOL into the insertion device, and expelling the IOL into the eye. The professional must not drop the IOL, or damage the IOL by improperly folding it. Next, the professional must properly insert the folded IOL into the delivery device without damaging it. The IOL must be positioned in the insertion device in the proper orientation so that the IOL and associated haptics are not damaged during the process of expelling the IOL into the eye.

At all times, the professional must maintain the sterility of the IOL. Once the sterility of the IOL is broken, it must be discarded. Additionally, the folding and inserting process can be time consuming.

In view of the above problems recognized by the inventors, it is an object of the present invention to fold and insert an IOL into a lens delivery device without damaging the IOL.

It is another object of the present invention to fold and insert an IOL into a lens delivery device while maintaining the sterility of the IOL.

It is another object of the present invention to fold and insert an IOL into a lens delivery device quickly and without the need for special training or dexterity skills.

According to the present invention, a container that stores an IOL also functions as an "automatic" IOL folding and inserting device. The sterile IOL is positioned within the container. The container also includes a lens folding mechanism. The container may be coupled with a lens delivery device.

In one embodiment, the IOL is folded and inserted into a lens delivery device in a predetermined orientation during the coupling process. In another embodiment, after the lens delivery device is coupled with the container, a manipulation of the container folds and inserts the IOL into the lens delivery device in a predetermined orientation. In either embodiment, the sterility of the IOL is maintained, and the lens is folded and inserted in a manner that minimizes the possibility of damaging the IOL.

The present invention provides a number of advantages. Transfer and folding of the IOL is performed quickly and without the need for specialized training or skills. The IOL is never "directly" handled by a person (e.g., by forceps) minimizing the possibility of damaging the lens from mishandling, improper folding, or improper insertion into the lens delivery device. The IOL is always folded and positioned in the lens insertion device in a predetermined orientation.

Also, the sterility of the IOL is maintained. Finally, the lens container serves the dual purpose of (1) storing the IOL, and (2) folding and inserting the IOL into the lens delivery device. Other advantages and features will become apparent from the following description and claims.

DESCRIPTION OF THE PREFERRED EMBODIMENTS

Figure 1A:
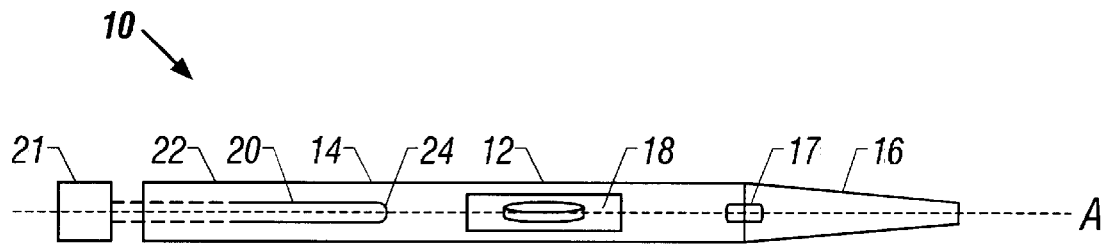
FIG. 1A is a plan view of a lens insertion device.
Figure 1B:
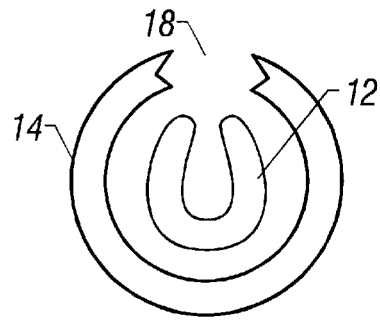
FIG. 1B is a cross-sectional view of a lens insertion device.

FIGS. 1A–1B show an IOL insertion device 10 used to insert an IOL 12 into a patient's eye. Insertion device 10 includes sleeve 14, nozzle 16, and mating tab 17. Nozzle 16 may be a separate component removably connected with sleeve 14, or a tapered extension of sleeve 14. Sleeve 14 includes a lens receiving slot 18 for receiving an IOL 12. IOL 12 is folded inside sleeve 14. IOL 12 is folded roughly in half along the longitudinal axis of sleeve 14 (shown by dashed line A) so that the two halves of the concave surface of IOL 12 generally face each other, as shown in FIG. 1B.

Figure 1C:
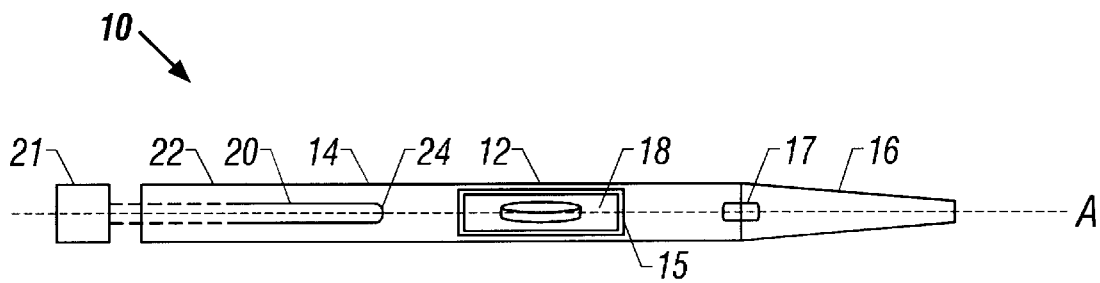
FIG. 1C is a plan view of another embodiment of a lens insertion device.

FIG. 1C shows another embodiment of an insertion device 10. A removable cartridge 15 is positioned in sleeve 14. Removable cartridge includes a lens receiving slot 18 for receiving an IOL 12. In another embodiment, all or a distal part of sleeve 14 may be disposable.

IOL insertion device 10 also includes a retractable lens piston 20 controlled by an actuator 21. In one embodiment, actuator 21 is a motor. In another embodiment, piston 20 may include an extension which allows the surgeon to control the movement of piston 20 manually. When nozzle 16 is properly positioned in a patient's eye through an incision, piston 20 moves along longitudinal axis A of sleeve 14, pushing IOL 12 through nozzle 16 until IOL 12 is expelled into the eye. Piston 20 is then retracted toward the proximal end 22 of sleeve 14.

Piston 20 may have a rounded lens-contacting tip 24 as shown in FIG. 1A, or other appropriate shape (e.g., flat or ballooned) to push IOL 12 into the patient's eye without damaging IOL 12. Tip 24 may also include a groove for receiving the haptics so that the haptics are not damaged during the insertion process. One example of an IOL insertion device 10 is disclosed in co-pending application Ser. No. 08/275,835, incorporated herein by reference to the extent necessary for an understanding of the present invention.

IOL 12 is transferred from a storage container into sleeve 14. Although IOL 12 is foldable (as shown in FIGS. 1A–1B), it should be handled carefully throughout the transfer process to avoid even the slightest damage, which may degrade the performance of IOL 12. IOL 12 is a sterile implant and cannot be dropped or otherwise mishandled in a way that compromises its sterility. IOL 12 must be carefully folded so as to avoid tearing, permanent deformation, or microfractures. Tearing and permanent deformation obviously can degrade the performance of IOL 12. Microfractures can also degrade the optical performance of IOL 12 and are difficult to detect by the IOL implantation team.

Failure to position IOL 12 in sleeve 14 through slot 18 in the proper orientation may cause IOL 12 to bind or jam when being pushed through nozzle 16. Such an incident may not only damage IOL 12 or the associated haptics, but also prevent the reuse of sleeve 14 and damage actuator 21 or piston 20.

The present invention is directed to a dual-purpose IOL storage container. The container stores the IOL in a sterile environment from packaging until the IOL is to be implanted. The container also functions as a sterile, "no-touch" lens folding system. The IOL is folded and transferred to an IOL insertion device 10 automatically and in a predetermined orientation, while maintaining the sterility of IOL 12.

One embodiment of a lens storage and folding container is shown in FIGS. 2A–2G. A housing 30 includes opposed first and second surfaces 32, 34, connected by opposed support surfaces 36, 38 and 40, 42, respectively, defining an enclosed storage chamber 44. Housing 30 is made of medical grade plastic or other material suitable for storing a sterile implant.

Support surface 40 includes an inner wall 45 which defines an aperture 46. Aperture 46 has a width and height suitable for receiving nozzle 16 and sleeve 14 of IOL insertion device 10. Aperture 46 may be covered by a tear-away panel 48 (shown in dotted line). In another embodiment, panel 48 may be permanently affixed to support surface 40, covering aperture 46, and made of a thin-film material. Nozzle 16 is then used to puncture panel 48 as insertion device 10 is inserted into chamber 44.

Figure 2A:
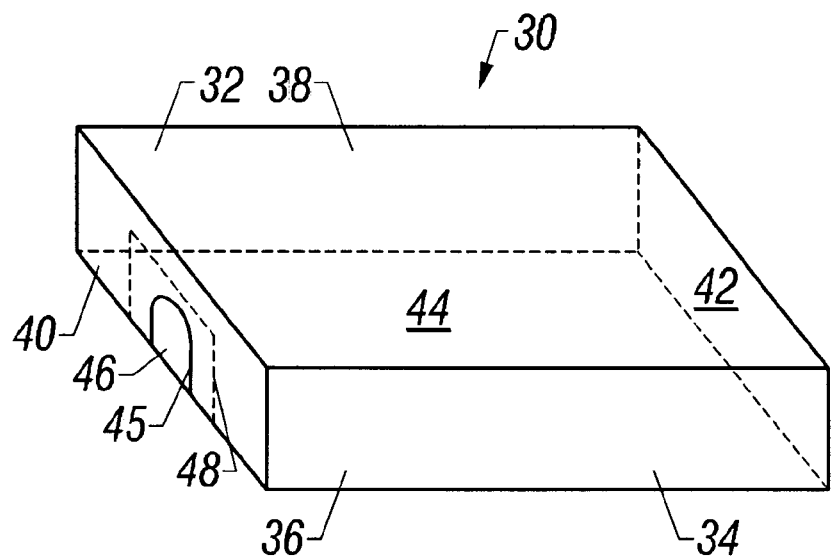
FIG. 2A is a perspective view of an embodiment of a lens storage and folding apparatus.
Figure 2B:
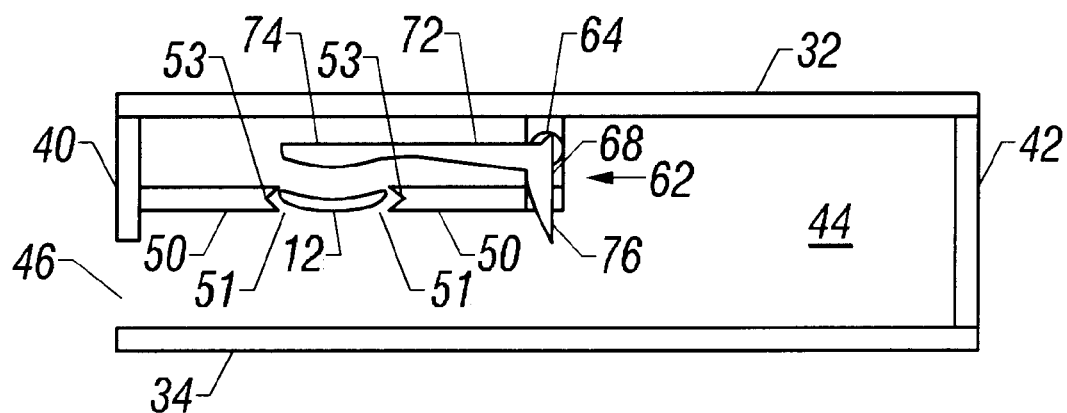
FIG. 2B is a side view of an embodiment of a lens storage and folding apparatus.

FIG. 2B is a side view of chamber 44. A lens platform 50 is positioned in chamber 44. Lens platform 50 supports IOL 12 during storage. In one embodiment, lens platform 50 extends from support surface 40, generally parallel to first and second surfaces 32, 34. Lens platform 50 may be connected to surface 40 by a cantilever mounting. In other embodiments, lens platform 50 may be suspended from first surface 32, supported by legs extending from second surface 34, supported by support surfaces 36, 38, or a combination thereof.

Figure 2C:
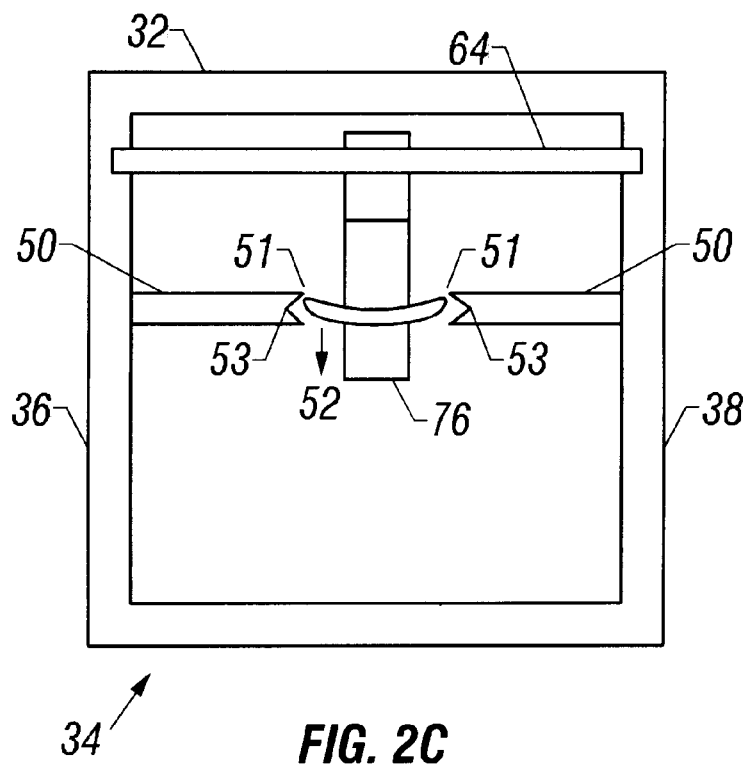
FIGS. 2C–2D are cross-sectional views of embodiments of a lens storage and folding apparatus.

FIG. 2C shows lens platform 50 including an inner wall 51, which defines a lens folding aperture 52. A V-shaped groove 53 in wall 51 supports the periphery of IOL 12, while a central portion of IOL 12 is suspended across aperture 52. Lens platform 50 may be made of any material suitable for supporting a sterile implant. IOL 12 is positioned in groove 53 with haptics oriented so that when IOL 12 is folded, the haptics will be in a desired position for insertion into sleeve 14.

Figure 2D:
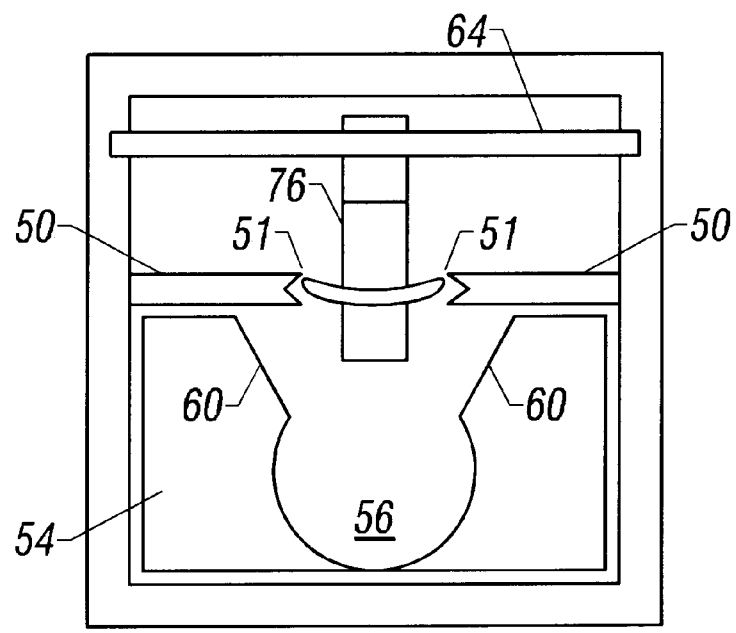
Figure 2E:
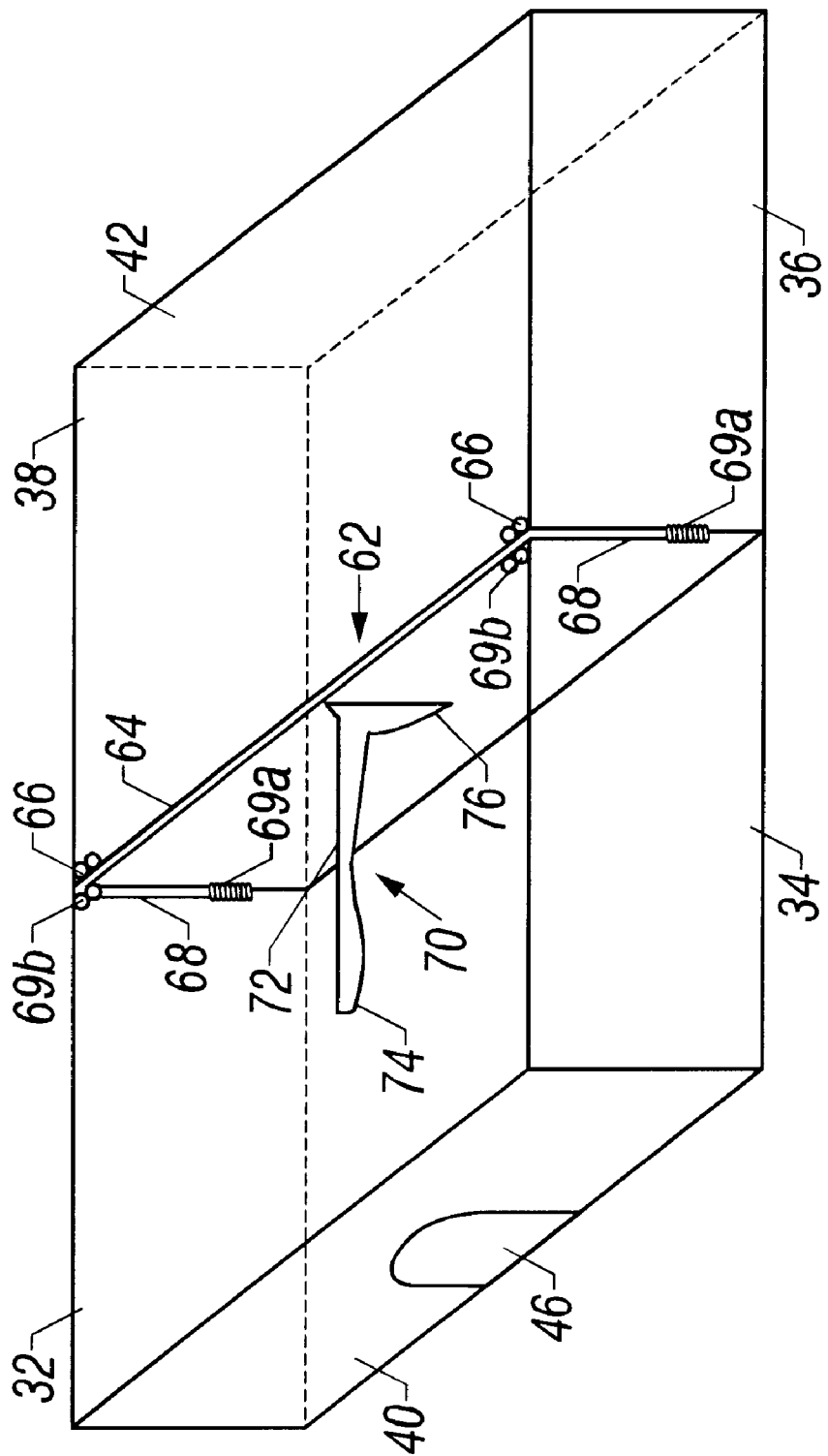
FIG. 2E is a perspective view of an embodiment of a lens storage and folding apparatus showing the lens folding system.

In another embodiment, shown in FIG. 2D, mold 54 is positioned between lens platform 50 and second surface 34. Mold 54 defines a longitudinal channel 56 extending from aperture 46 at support surface 40 to support surface 42 for receiving sleeve 14. Additionally, mold 54 defines inwardly-sloped, opposed upper surfaces 60, which generally define a funnel shape. Mold 54 may be removably positioned in chamber 44 or integrally formed with housing 30.

Lens folding system 62 is also positioned in chamber 44. Lens folding system 62 includes a support bar 64 which extends from support surface 36 to support surface 38. In other embodiments, support bar 64 is positioned by arms extending from first surface 32, second surface 34, or both. The ends 66 of support bar 64 slidably fit in opposed grooves 68 on support surfaces 36, 38, allowing support bar 64 to rotate as shown by arrow B and move vertically (shown by arrow C) as allowed by grooves 68.

An L-shaped lens folding member 70 is connected to support bar 64. Lens folding member 70 includes a folding segment 72 having a lens folding tip 74, and an actuating segment 76 positioned at a right angle to folding segment 72. Lens folding member 70 is positioned on support bar 64 within chamber 44 so that folding segment 72 is positioned during storage between platform 50 and first surface 32, and actuating segment 76 extends from support bar 64 toward second surface 34. Also, lens folding tip 74 is positioned between IOL 12 on platform 50 and first surface 32.

In one embodiment, support bar 64 is biased in grooves 68 toward first surface 32, e.g., by spring members 69A positioned in grooves 68. Additionally, one or more torsional springs 69B may be connected with support bar 64 to bias folding segment 72 between platform 50 and first surface 32.

Figure 2F:
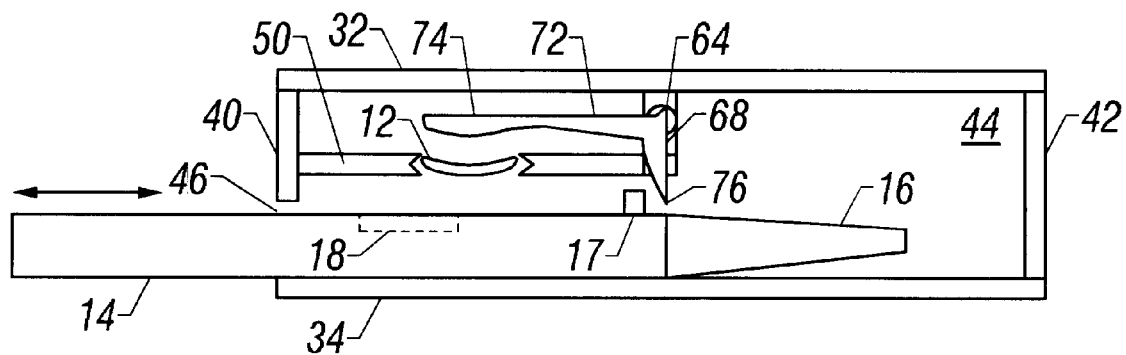
FIGS. 2F–2G are side views of a lens insertion device receiving a lens from an embodiment of a lens storage and folding apparatus.
Figure 2G:
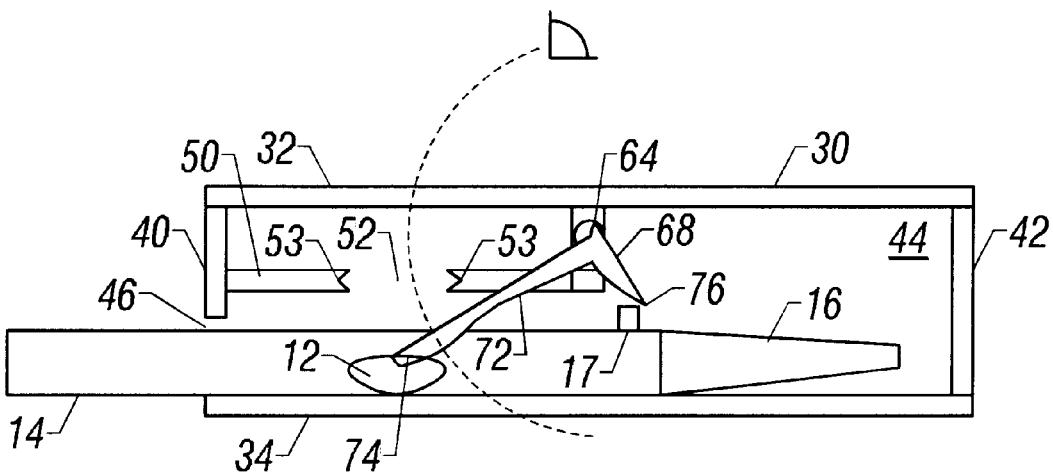

FIGS. 2F and 2G show the process of folding and inserting IOL 12 into sleeve 14. Nozzle 16 is inserted into chamber 44 through aperture 46, and extended toward wall 42. Sleeve 14 is oriented relative to housing 30 so that tab 17 is aligned to meet actuating segment 76. Tab 17 catches actuating segment 76, overcoming the spring bias against support bar 64, and initially moving support bar 64 in groove 68 toward second surface 34. The movement of support bar 64 causes lens folding tip 74 to move along the path shown by line D. Lens folding tip 74 contacts the central portion of IOL 12, causing IOL 12 to fold through aperture 52, then through slot 18 into sleeve 14. The slope of walls 60 assist folding IOL 12 in the embodiment of FIG. 2D. In either embodiment, IOL 12 is folded in a predetermined orientation without excessive stress, thereby preventing tearing, permanent deformation, or microfractures.

Once IOL 12 is folded and positioned in sleeve 14, sleeve 14 is then drawn back out of chamber 44 through aperture 46 in a reciprocal motion. As sleeve 14 exits aperture 46, folding segment 72 is forced out of slot 18 and back toward its storage position above aperture 52 by torsional spring 69B. Actuating segment 76 moves back toward its storage position, and the spring bias moves support bar 64 toward first surface 32.

Figure 3:
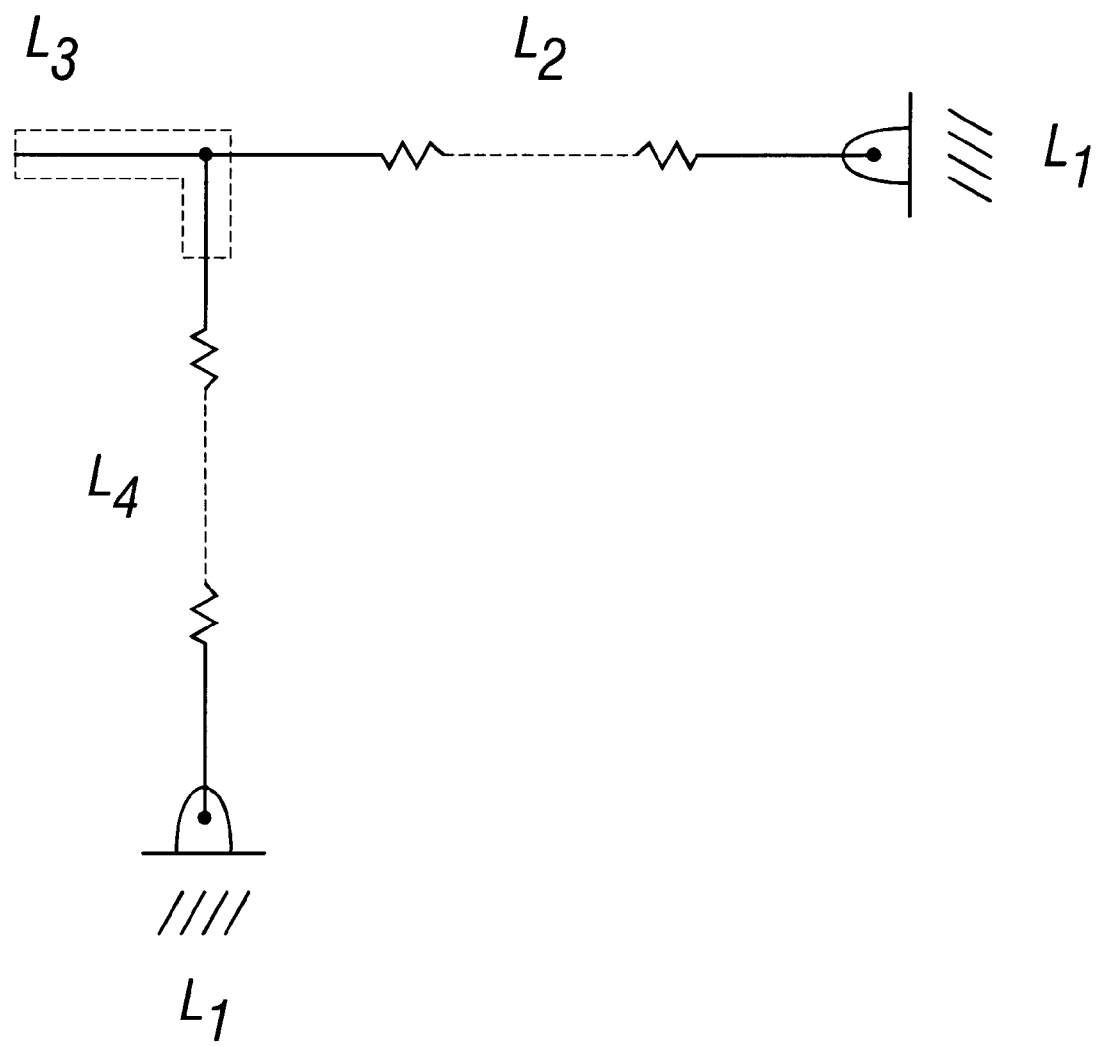
FIG. 3 is a diagram of a four-bar mechanical linkage representative of the lens folding system of an embodiment of a lens storage and folding apparatus.

FIG. 3 shows a diagram of a four-bar mechanical linkage which is representative of lens folding system 62. Link L1 provides the ground for the four-bar linkage circuit. Link L2, represented as having an infinite length, corresponds to support bar 64 movable in grooves 68. Link L3 corresponds to folding and actuating segments 72, 76, respectively, of folding member 70. Link L4, also represented as having an infinite length, corresponds to mating tab 17 acting on actuating segment 76. The configuration of lens folding system 62 is commonly known as a double-slider mechanism.

When a force, such as tab 17, acts on actuating segment 76, support bar 64 initially moves towards second surface 34 causing folding segment 72, and more specifically folding tip 74, to move on a generally linear path, shown by arrow D in FIG. 2F. The four-bar linkage provides an efficient way to use the energy of inserting nozzle 16 and sleeve 14 into chamber 44 to actuate lens folding tip 74, folding IOL 12 through aperture 52 and into sleeve 14. IOL 12 is automatically inserted into sleeve 14 in a known position by precisely timed movement of the four-bar linkage. IOL 12 is positioned in sleeve 14 without damage. The arrangement minimizes the need for any special training or skills by the person loading IOL 12. The sterility of IOL 12 is also maintained.

FIGS. 4A–4D show another embodiment of a lens storage and folding container. A housing 100 includes a first surface 102 and opposed second surface 103. Opposed side surfaces 104, 106 connect first surface 102 with second surface 103. Opposed side surfaces 108, 110 connect with second surface 103 and extend to the edges of first surface 102, but do not connect with first surface 102 or side surface 106. The combination defines a storage chamber 112.

First surface 102 includes hinge 114 extending from edge 116 of first surface 102 adjacent the top of side surface 108 to edge 118 of first surface 102 adjacent the top of side surface 110. Hinge 114 divides first surface 102 into first and second planar members 120, 122, respectively. Second planar member 122 includes a generally U-shaped cutout, defining a lens folding tab 124 which extends from first planar member 120 at hinge 114. Hinge 114 may be a flexure line dividing first surface 102.

First surface 102 and side surface 106 are not connected with side surfaces 108, 110. Therefore, three additional hinges are defined. Hinge 125 is formed by the connection of the adjacent edges of second planar member 122 and side surface 104. Hinge 126 is formed by the connection of the adjacent edges of first planar member 120 and side surface 106. Hinge 127 is formed by the connection of the adjacent edges of side surface 106 and second surface 103. The combination of hinges 114, 125, 126, 127 form a four-bar linkage.

Figure 4A:
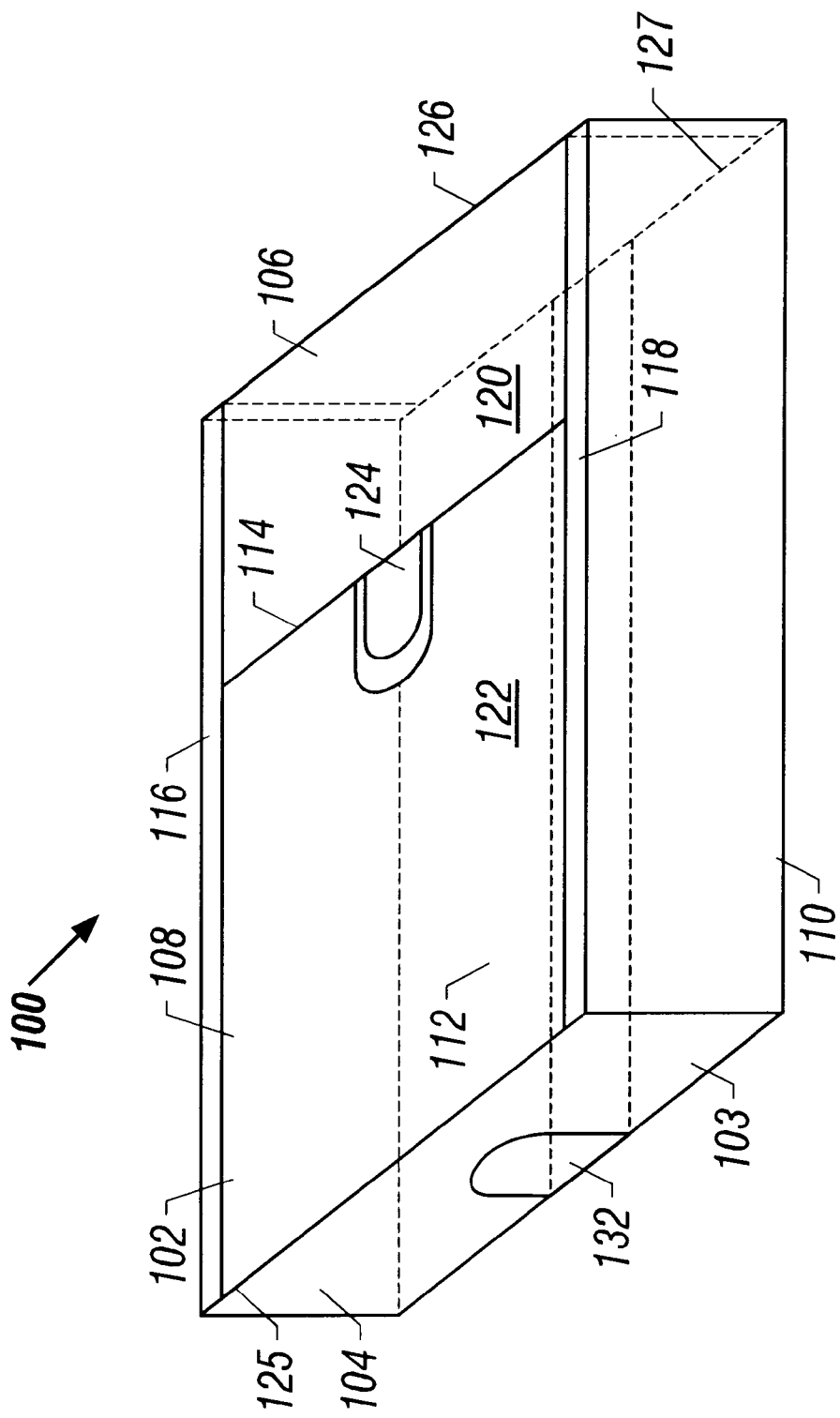
FIGS. 4A–4B are perspective views of an embodiment of a lens storage and folding apparatus.
Figure 4B:
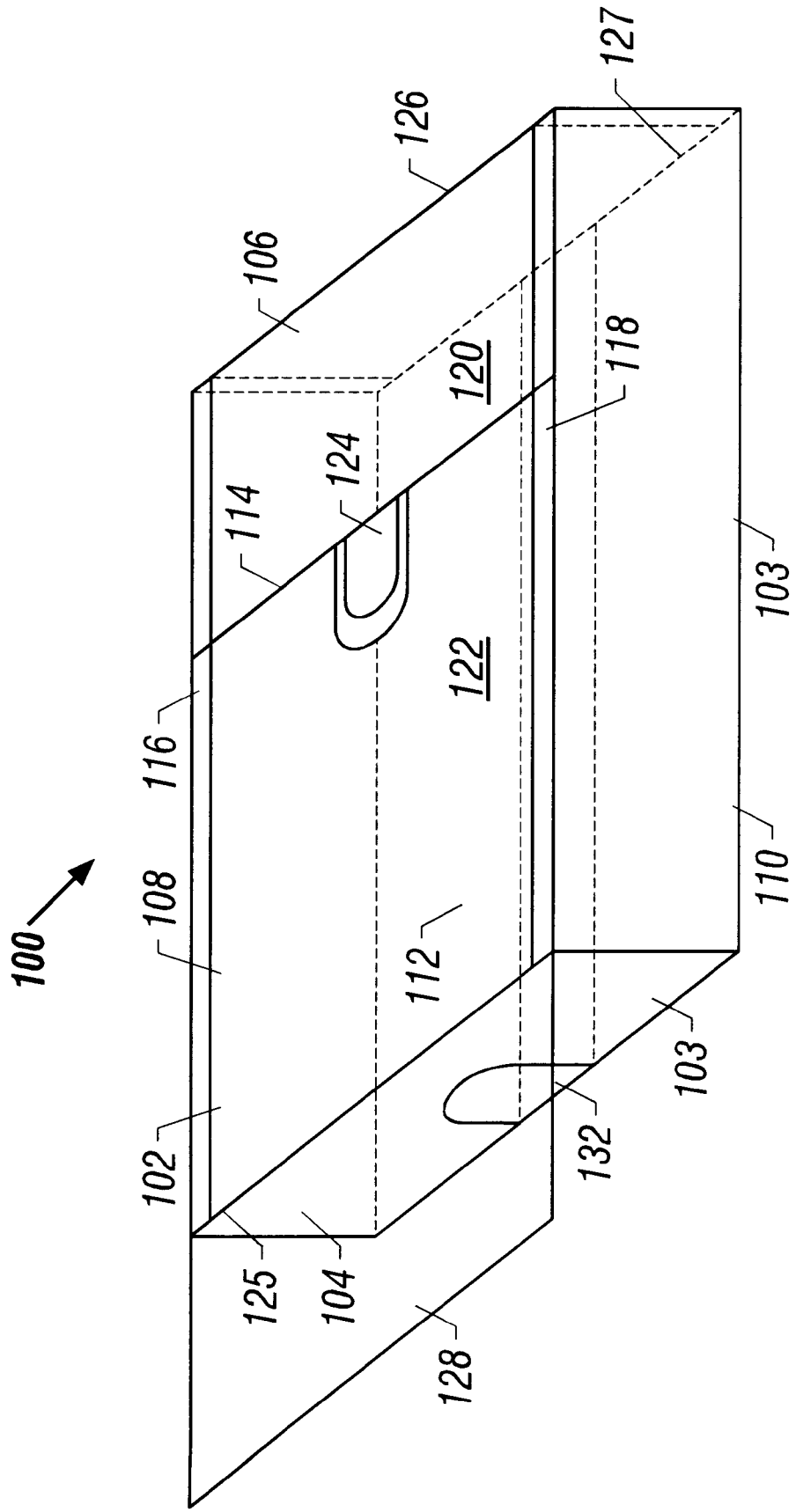

In another embodiment, shown in FIG. 4B, leverage tab 128 extends from housing 100 adjacent hinge 125.

Figure 4C:
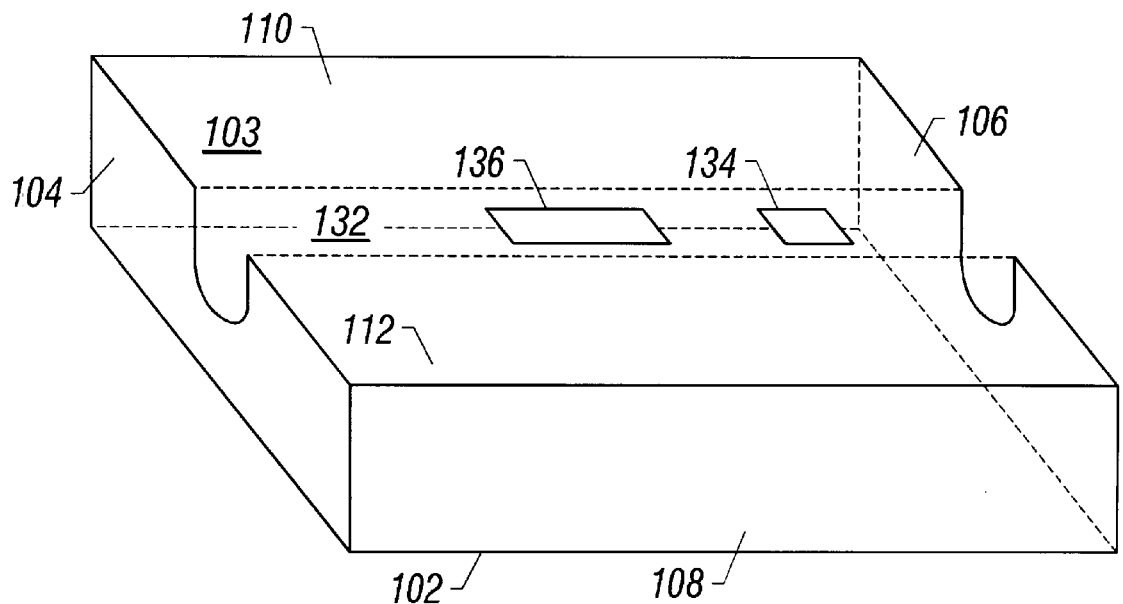
FIG. 4C is perspective view of the second surface of an embodiment of a lens storage and folding apparatus.

FIGS. 4A–4C show sleeve-receiving channel 132 extending along second surface 103 from side surface 104 to side surface 106. Sleeve-receiving channel 132 is semi-circular and has a diameter slightly larger than the diameter of sleeve 14 to provide a stable coupling with sleeve 14. Sleeve-receiving channel 132 includes a tab receiving slot 134 for receiving tab 17 of a lens insertion device 10. Tab 17 is positioned on sleeve 14 so that when tab 17 is positioned in tab receiving slot 134, lens transfer slot 136 aligns with lens receiving slot 18. Therefore, the coupling of sleeve 14 with housing 100 defines a precise orientation of sleeve 14 relative to housing 100 for the folding and transfer of IOL 12 into sleeve 12.

In another embodiment, clamps or other locking devices may be used to couple lens insertion device 10 with channel 132.

Figure 4D:
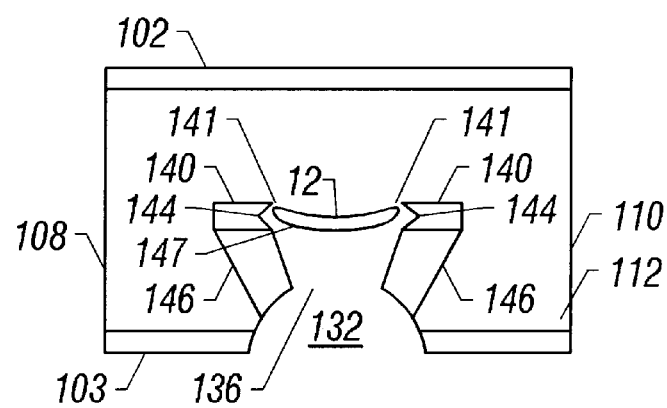
FIG. 4D is a cross-sectional view of an embodiment of a lens storage and folding apparatus.

FIG. 4D shows lens platform 140 positioned in chamber 112 for supporting IOL 12 as described above regarding the embodiments of FIGS. 2A–2G. Once again, platform 140 may be anchored by a cantilever mount, suspended from first surface 102 or supported from second surface 103 (as shown). Platform 140 includes an inner wall 141 which defines an aperture 142. IOL 12 is held in place by a V-shaped groove 144 in wall 141 and extends across aperture 142. In one embodiment, opposed tapered surfaces 146 extend from lens platform 140 to lens transfer slot 136, serving to fold IOL 12 in the appropriate orientation without excessive stress on IOL 12.

Figure 5A:
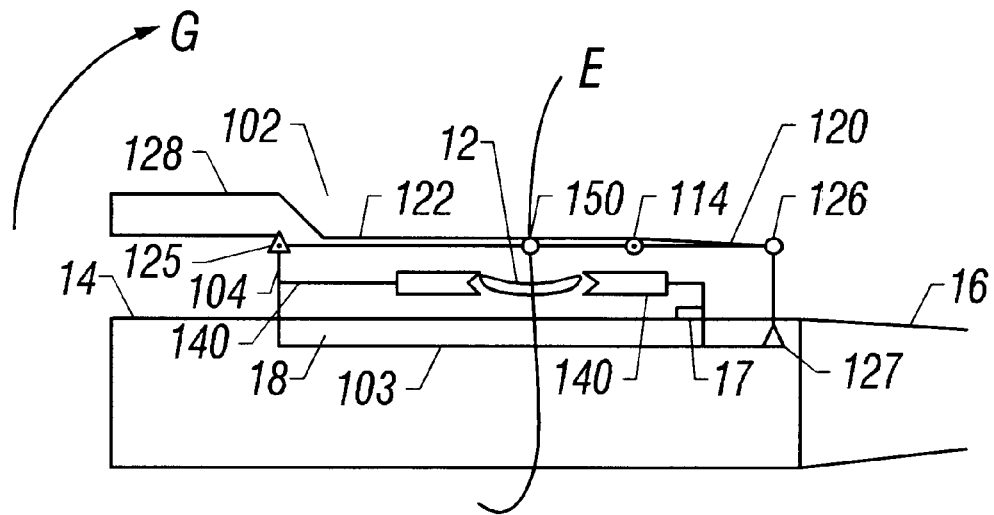
FIGS. 5A–5B are side views of a lens insertion device receiving a lens from an embodiment of a lens storage and folding apparatus.
Figure 5B:
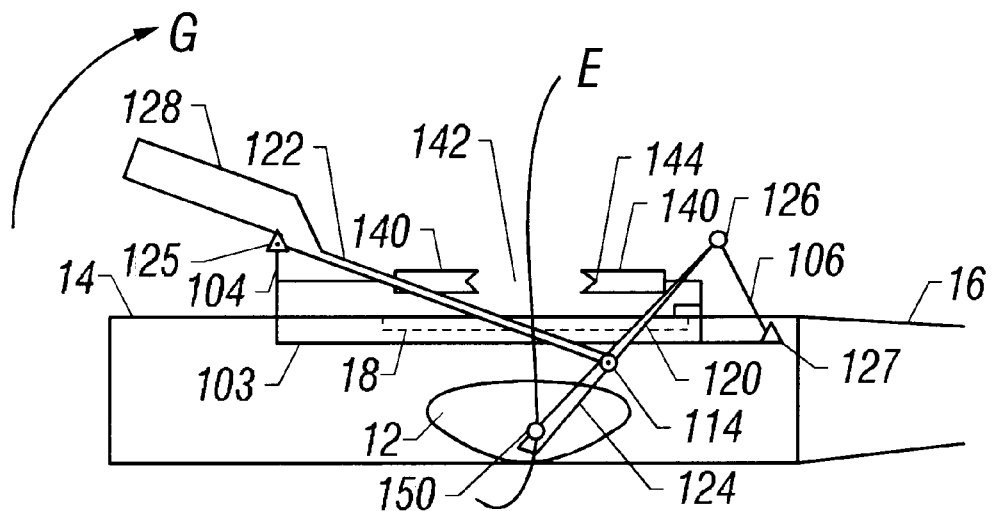

FIGS. 5A–5B show the lens storage and folding container of FIGS. 4A–4D in operation. Housing 100 is coupled with lens insertion device 10 and the housing surfaces 102, 103, 104, and 106 form a four-bar linkage and function as a lens folding system. The ground or first link corresponds to second surface 103 and side surface 104. Side surface 106 corresponds to the second link. First member 120 and lens folding tab 124 correspond to the third link. Finally, second planar member 122 corresponds to the fourth link.

To actuate the four-bar linkage for folding IOL 12 into sleeve 14, a user can depress either first member 120 or second member 122 toward second plate 103, or move leverage bar 128 in the direction of arrow G (for the embodiment of FIG. 4B). First surface 102 flexes at hinge 114, driving the adjacent ends of first and second members 120, 122, toward second surface 103. Second member 122 flexes as hinge 125, and side surface 106 flexes at hinge 127. The movement of first member 120 causes tip 150 of lens folding tab 124 to move along path E.

Path E is generally linear as tip 150 moves through aperture 142, folding and pushing IOL 12 through lens transfer slot 136, through slot 18, and into sleeve 14. It should be noted that hinge 126 may remain generally fixed, defining about a ninety degree angle between first member 120 and support surface 106, which provides a simplified four-bar linkage. Therefore, hinge 126 may not be necessary, simplifying the construction of housing 100.

Using the lens storage and folding container of FIGS. 4A–4D requires no special training. The linkage lengths, passageway shapes, tab lengths are all selected to define a precise orientation in order to fold IOL 12 into sleeve 14 without tearing, permanently deforming, or fracturing IOL 12.

Once the folded IOL 12 is seated within sleeve 14, the user releases first or second member 120, 122, or leverage bar 128, allowing tab 124 to return along linkage path E, exiting sleeve 14 through slot 18. Housing 100 can then be removed from sleeve 14, and IOL 12 is properly positioned within sleeve 14 for insertion into the patient's eye.

Figure 6:
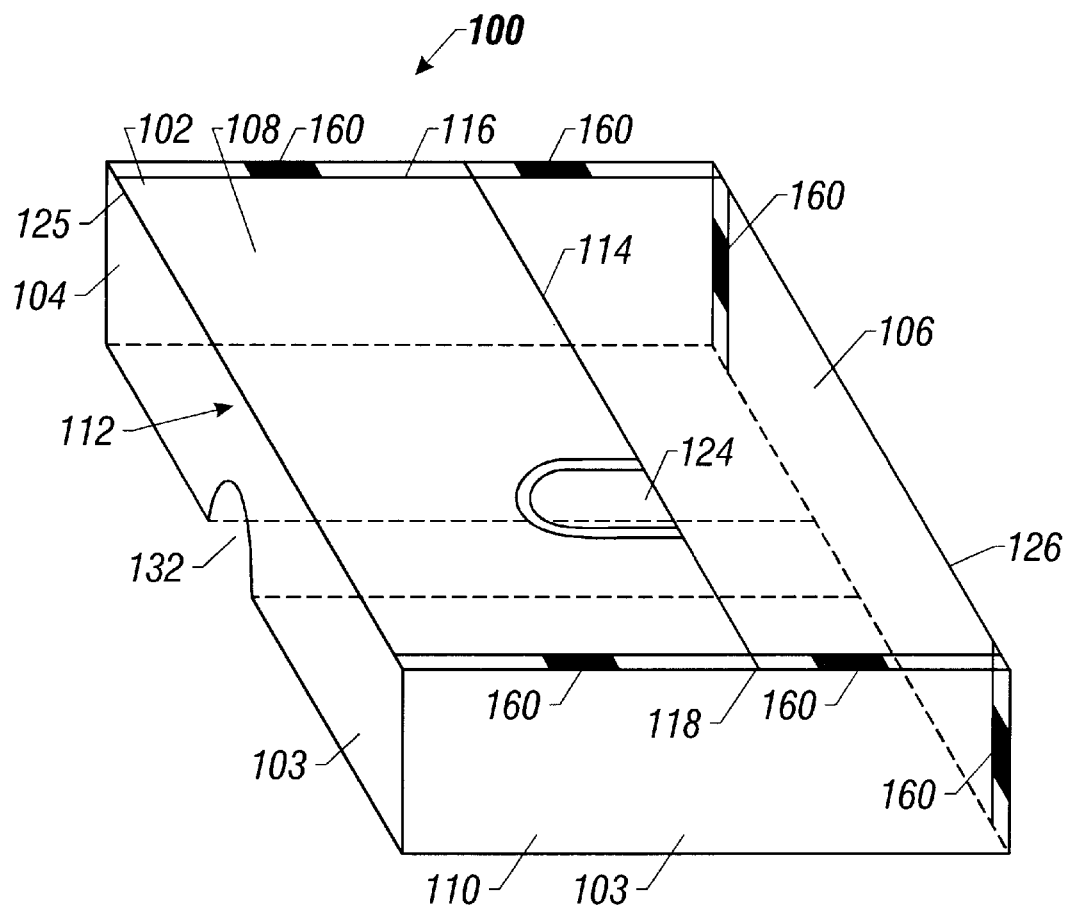
FIG. 6 is a perspective view of an embodiment of a lens storage and folding apparatus.

In another embodiment, shown in FIG. 6, first surface 102 and side surface 106 are connected with side surfaces 108, 110 by breakable tabs 160. During storage, breakable tabs 160 provide rigidity to housing 100 and reduce the likelihood that the folding mechanism of housing 100 will be accidentally actuated. Tabs 160 are designed so that the force required to break the tabs is large enough to minimize accidental actuation, but not so large as to result in uncontrolled actuation that could damage the IOL.

In another embodiment, first surface 102 is made of a deformable material. This eliminates the need for the several hinges in the embodiment described above. Lens folding tab 124 is actuated by placing pressure on the first surface 102 adjacent lens folding tab 124.

In the embodiments discussed above, the lens storage and folding device is described as docking with sleeve 14. In other embodiments, the lens storage and folding device may dock also with removable cartridge 15 or a disposable sleeve 14. In the first instance, IOL 12 is loaded into cartridge 15, and cartridge 15 is loaded into lens insertion device 10. In the second instance, IOL 12 is loaded into disposable sleeve 14, and disposable sleeve 14 is coupled with the remaining portions of lens insertion device 10.

Other embodiments are within the scope of the following claims.

What is claimed is:

1. A lens storage and folding apparatus, comprising:
   a housing having first and second generally opposed surfaces, support surfaces connecting at least a portion of the first and second surfaces, which define a cavity; and a lens-holding platform positioned in the cavity and connected with at least one of the surfaces;
   wherein at least the first surface is movable and comprises a lens folding system;
   wherein the support surfaces comprise a first pair of generally opposed side surfaces connected with the first and second surfaces, and a second pair of generally opposed side surfaces connected with the second surface; and
   wherein the first surface includes a first hinge dividing the first surface into first and second members.

2. The apparatus of claim 1 wherein the platform includes an inner wall defining a lens aperture.

3. The apparatus of claim 2 wherein the inner wall includes a groove.

4. The apparatus of claim 1 further comprising a second hinge connecting the second member with the first side surface of the first pair of opposed side surfaces, and a third hinge connecting the second surface with the second side surface of the first pair of opposed side surfaces.

5. The apparatus of claim 4 wherein the second hinge connects an edge of the second member with an edge of the first side surface of the first pair of opposed side surfaces, and the third hinge connects an edge of the second surface with an edge of the second side surface of the first pair of opposed side surfaces.

6. The apparatus of claim 4 further comprising a fourth hinge connecting the first member with the second side surface of the first pair of opposed side surfaces.

7. The apparatus of claim 1 comprising a leverage bar extending from one of the support surfaces.

8. A lens storage and folding apparatus, comprising:
   a housing having first and second generally opposed surfaces, support surfaces connecting at least a portion of the first and second surfaces, which define a cavity; and a lens-holding platform positioned in the cavity and connected with at least one of the surfaces;
   wherein at least the first surface is movable and comprises a lens folding system; and
   wherein the second surface includes a channel extending between generally opposed support surfaces.

9. The apparatus of claim 2 further comprising a lens transfer slot positioned on one of the surfaces, the lens transfer slot being generally aligned with the lens aperture.

10. The apparatus of claim 9 further comprising a lens insertion device removably coupled with the transfer-slot surface.

11. The apparatus of claim 10 further comprising a lens receiving slot, the lens receiving slot being aligned with the lens transfer slot when the lens receiving device is coupled with the lens-transfer surface.

12. The apparatus of claim 1 further comprising a lens folding tab extending from the first member adjacent the first hinge.

13. The apparatus of claim 12 further comprising breakable tabs connecting the second pair of side surfaces with the first surface.

14. The apparatus of claim 12 further comprising breakable tabs connecting the second pair of side surfaces with at least one of the first pair of side surfaces.

* * * * *